(12) United States Patent
Colpan

(10) Patent No.: US 6,609,618 B2
(45) Date of Patent: Aug. 26, 2003

(54) DEVICE FOR THE ISOLATION OF CELL COMPONENTS SUCH AS NUCLEIC ACIDS FROM NATURAL SOURCES

(75) Inventor: Metin Colpan, Essen-Kettwig (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 09/900,199

(22) Filed: Jul. 9, 2001

(65) Prior Publication Data

US 2001/0047966 A1 Dec. 6, 2001

Related U.S. Application Data

(63) Continuation of application No. 08/253,152, filed on Jun. 2, 1994, now Pat. No. 6,277,648, which is a continuation-in-part of application No. PCT/EP92/02774, filed on Dec. 1, 1992.

(30) Foreign Application Priority Data

Dec. 2, 1991 (DE) ........................... P 41 39 664

(51) Int. Cl.[7] ............................................. B01D 29/00
(52) U.S. Cl. .................... 210/489; 210/488; 210/502.1; 210/503; 422/101
(58) Field of Search ................. 210/489, 496, 210/502.1, 503, 510.1, 635, 644, 645, 649, 650, 651, 767, 800, 488; 436/177, 178; 435/2, 6, 287.2, 288.6; 422/99, 101; 55/487, 488, 523, 527

(56) References Cited

U.S. PATENT DOCUMENTS

| | | | |
|---|---|---|---|
| 956,832 A | 5/1910 | Seitz | |
| 2,114,748 A | 4/1938 | Prausnitz | 210/205 |
| 3,935,111 A * | 1/1976 | Bentley | 210/446 |
| 4,033,881 A * | 7/1977 | Pall | 210/491 |
| 4,087,363 A * | 5/1978 | Rosemeyer et al. | 210/342 |
| 4,141,887 A * | 2/1979 | Seufert | 210/787 |
| 4,303,530 A * | 12/1981 | Shah et al. | 210/651 |
| 4,431,545 A * | 2/1984 | Pall et al. | 210/650 |
| 4,699,717 A * | 10/1987 | Riesner et al. | 210/656 |
| 4,734,192 A * | 3/1988 | Champion et al. | 210/489 |
| 4,797,213 A * | 1/1989 | Parisius et al. | 210/651 |
| 4,797,260 A * | 1/1989 | Parker | 422/101 |
| 4,828,705 A * | 5/1989 | Thakore et al. | 210/636 |
| 4,925,572 A | 5/1990 | Pall | 210/767 |
| 4,935,142 A | 6/1990 | Sternberg | 210/645 |
| 4,935,342 A * | 6/1990 | Seligson et al. | 435/6 |
| 4,976,861 A * | 12/1990 | Pall | 210/508 |

(List continued on next page.)

FOREIGN PATENT DOCUMENTS

| | | |
|---|---|---|
| EP | 0 364 173 | 4/1990 |
| EP | 0 406 485 | 1/1991 |
| EP | 0431905 | 6/1991 |
| EP | 0471910 | 2/1992 |
| WO | 9200132 | 1/1992 |

OTHER PUBLICATIONS

Filtron Technology Corporation—Catalogue—Jan. 1991.
Takahatu Mizutani, "Adsorption Chromatography of Nucleic Acids on Silicone–Coated Porous Glass", J. Biochem. vol. 94, (1983), pp. 163–169.
ISBN 4–06=129832–1 (1) (KS), NDC 579, 325 p. 22 cm., B. Hagiwara and K. Hashimoto (1974) (with English language translation).

*Primary Examiner*—John Kim
(74) *Attorney, Agent, or Firm*—Jacobson Holman PLLC

(57) ABSTRACT

Described is a method of isolating cell components, such as nucleic acids, from natural sources by filtering a sample of the digested natural sources such as cells or cell fragments. The method is characterized in that the sample is passed through a filter, the pore size of which decreases in the direction of flow of the sample through the filter.

4 Claims, 7 Drawing Sheets

U.S. PATENT DOCUMENTS

| | | | |
|---|---|---|---|
| 5,009,759 A | * | 4/1991 | Serwer et al. |
| 5,057,426 A | * | 10/1991 | Henco et al. ................ 435/270 |
| 5,076,933 A | * | 12/1991 | Glenn et al. ................. 210/651 |
| 5,078,853 A | * | 1/1992 | Manning et al. .............. 436/71 |
| 5,092,989 A | * | 3/1992 | Steen .......................... 210/85 |
| 5,098,571 A | * | 3/1992 | Maebashi .............. 210/500.23 |
| 5,135,627 A | * | 8/1992 | Soane .................... 204/182.8 |
| 5,185,127 A | * | 2/1993 | Vonk ........................... 422/56 |
| 5,187,083 A | * | 2/1993 | Mullis .......................... 435/6 |
| 5,208,160 A | * | 5/1993 | Kikyotani et al. .......... 210/638 |
| 5,221,483 A | * | 6/1993 | Glenn et al. ................ 210/641 |
| 5,298,165 A | * | 3/1994 | Oka et al. ................... 210/645 |
| 5,407,581 A | * | 4/1995 | Onodera et al. ............ 210/654 |
| 5,427,664 A | * | 6/1995 | Stoev et al. ............. 204/182.3 |
| 5,466,781 A | * | 11/1995 | Dorin et al. ................ 530/351 |
| 5,490,937 A | * | 2/1996 | van Reis .................... 210/651 |
| 5,552,325 A | * | 9/1996 | Nochumson et al. ....... 436/177 |
| 5,578,459 A | * | 11/1996 | Gordon et al. ................. 435/6 |
| 5,660,984 A | * | 8/1997 | Davis et al. ................... 435/6 |

\* cited by examiner

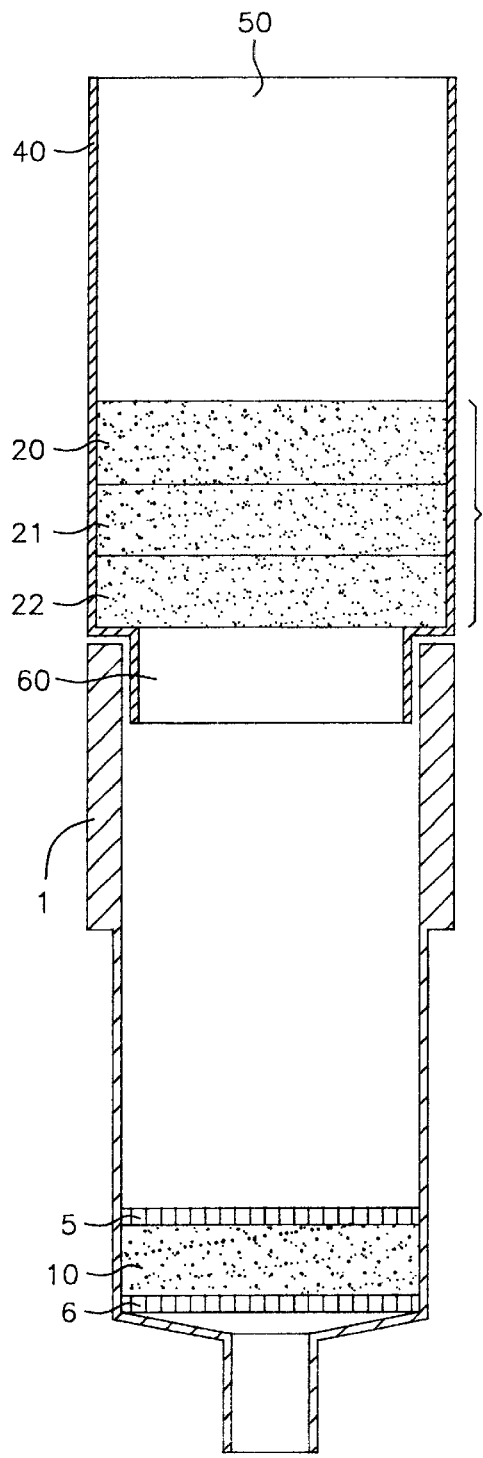
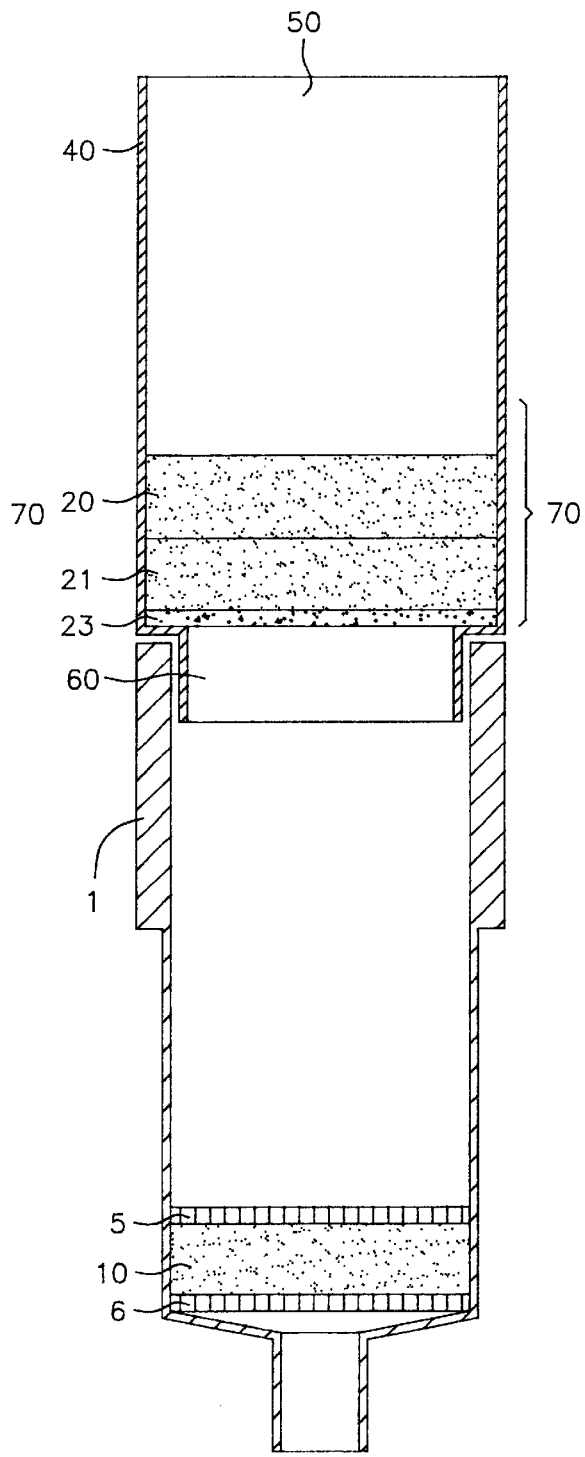

DEVICE FOR THE ISOLATION OF CELL COMPONENTS SUCH AS NUCLEIC ACIDS FROM NATURAL SOURCES

This is a continuation of Ser. No. 08/253,152, filed Jun. 2, 1994, U.S. Pat. No. 6,277,648, which is a continuation-in-part of PCT/EP92/02774, filed Dec. 1, 1992, the disclosures of which are incorporated herein by reference.

This invention is directed to a process for the isolation of components such as nucleic acids from natural sources by removing the digested natural sources such as cells or cell debris in a sample by filtration, and to a device for operating said process.

Frequently, in the preparation of cell components, particularly nucleic acids, the problem arises to separate the digested natural sources, from which the components are derived, from dissolved material. Removal of cells or cell debris is effected by centrifugation, whereby larger cell fragments or cells deposit as a pellet in the centrifugation tube. The cell components then are found in the supernatant and may be pipetted. Filtration procedures which are simpler per se were not capable of prevailing because the digested cells or fragments thereof either pass through the filter having too large a pore size and thus, give rise to turbidity and impurities in the filtrate or, when using filters with appropriately narrow pores, however, inevitable jamming results, so that purposeful preparation of the cell components is no longer possible.

Thus, the present invention is based on the problem of providing a process and creating a device by means of which centrifugation steps for the preparation of cell components from natural sources such as cells may be avoided by using filtration steps which are easier to handle.

The technical problem which the invention is based upon is solved by a process according to the features of claim 1. The subsequent subclaims are directed to preferred embodiments of the process according to the invention. The device of the invention presents the features of claim 10. The subsequent subclaims are directed to preferred embodiments of the device according to the invention.

Conventionally, in order to isolate the components from cells, the latter are digested first. In the preparation of nucleic acids, the cells have to be digested first by using enzymes such as, for instance, proteinase K and lysozyme, detergents such as SDS, Brij, Triton-X-100, Tween 20, and DOC, and chemicals such as sodium hydroxide, guanidine hydrochloride and guanidine isothiocyanate. Thereafter, the thus processed sample material is subjected to filtration, wherein the pore size of the filter used in filtration decreases in the direction of sample flow.

In a preferred embodiment, sample flow during filtration may be facilitated by applying elevated pressure or reduced pressure. However, due to the pore size configuration of the filter, passage of the sample to be filtrated through the filter is also possible solely by gravity as the driving force. Furthermore, in order to make the passage of sample through the filter more rapid, the sample may also be passed through the filter by centrifugation.

In particular, the process according to the invention is suitable for the preparation of plasmid DNA or genomic DNA having a size of from 1 to 50 kb.

As the filters which may be used in the process according to the invention, there are possible, in particular, those made of sintered polyethylene, polypropylene, polytetrafluoroethylene, glass, silica gel, aluminum oxide or packed diatomaceous earth, e.g., Cellit or silica gel, woven or bonded fleeces of polypropylene, polyester, glass fiber, and silica, as well as paper, pressed paper, fleeces made of paper or combinations thereof.

In a preferred embodiment of the process according to the invention, multiple samples are processed simultaneously and passed through appropriate devices advantageously adapted to microtitration systems.

BRIEF DESCRIPTION OF THE DRAWINGS

FIG. 3 shows an arrangement wherein the device of the invention consisting of a three layered filter is attached onto a cartridge and an anion exchanger material is present between two means.

FIG. 4 shows an analogous situation as in FIG. 3 with the filter head of the invention wherein a two-layered filter sealed by a hydrophobic interlayer is used.

The device of the invention for operating the process consists of a preferably cylindrical hollow body 40 having inlet and outlet openings 50, 60, and a filtration unit 70 arranged in the hollow body 40. For securing the filtration unit 70, common securing means may be used such as, for example, cementings, but also securing by frictional forces by jamming the filtration unit 70 in the hollow body 40.

Figure 1:
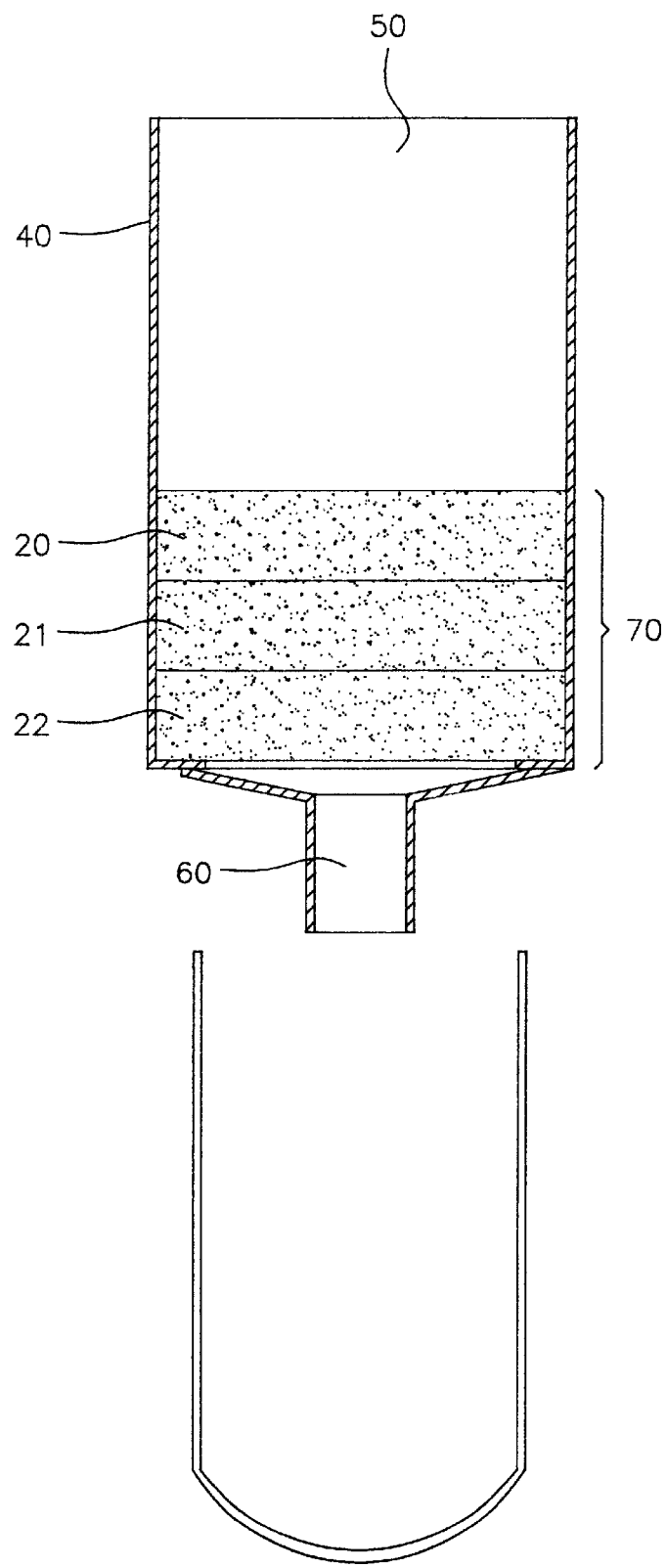
FIG. 1 shows a particularly preferred variant of the device of the invention wherein a filtration unit made of a three layered sheet is in a cylindrical hollow body.

The device of the invention consists of at least one filter with decreasing pore size as viewed in direction of the outlet opening 60. FIG. 1 shows a particularly preferred variant of the device of the invention, where in the preferably cylindrical hollow body 40, the filtration unit 70 is made of a three-layered sheet. Here, the top layer 20 preferably may have a pore size of from 100 to 300 $\mu$m, the second layer may have a pore size of from 30 to 100 $\mu$m, and the third layer may have a pore size of from 5 to 30 $\mu$m. As the materials which the single layers may consist of, there are possible, in particular, those made of sintered polyethylene, polypropylene, polytetrafluoroethylene, glass, silica gel, aluminum oxide or packed diatomaceous earth, e.g., Cellit or silica gel, woven or bonded fleeces of polypropylene, polyester, glass fiber, and silica, as well as paper, pressed paper, fleeces made of paper or combinations thereof. The pore size of the filter layer is in the range of from 5 $\mu$m to 500 $\mu$m at an overall filter layer thickness of from 0.1 to 10 mm.

In a particularly preferred embodiment, for example, the filter layer 20, 21 may consist of an inorganic material having the pore size gradation as specified, whereas the filter layer 22 may also consist of paper.

It may be advantageous to arrange an additional layer 23 in the hollow body 40, namely, above layer 20 or below layer 22, which prevents early penetration of the solution to be filtered into the filter, or flow of the solution out of the device of the invention. However, it is also possible to design layer 20 or layer 22 as a porous hydrophobic layer. Where the hydrophobic interlayer 23 is arranged above interlayer 20, it is advantageous when the pore size of this interlayer is not smaller than that of layer 20 beneath. With the other configuration, where the hydrophobic interlayer is arranged beneath layer 20, this requirement is not that critical.

Figure 2A:
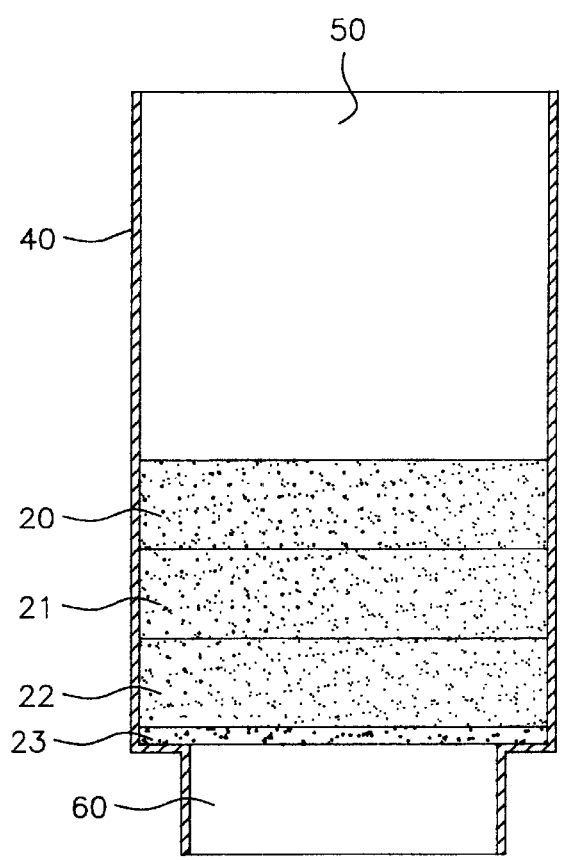
FIGS. 2a and 2b show the corresponding configuration with hydrophobic interlayer according to the preferred device of FIG. 1.
Figure 2B:
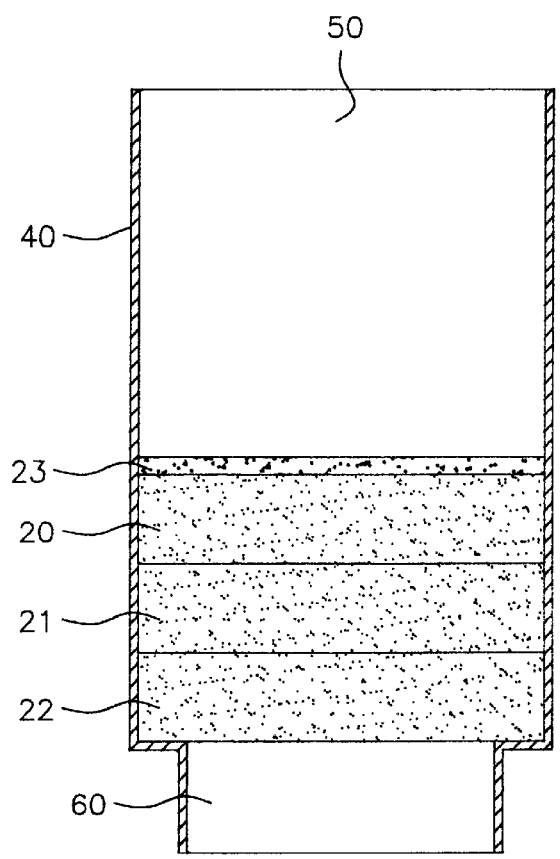

FIGS. 2a) and 2b) show the corresponding configuration with hydrophobic interlayer according to the preferred device of FIG. 1.

In another preferred embodiment, the device of the invention may be combined with further instruments necessary for nucleic acid preparation, namely, those as described in the parallel application P 41 39 664.

In said P 41 39 664, there are also described appropriate instruments, for example. The anion exchanger is embedded in a membrane (3M Empore Membrane). These systems are commercially available under the name of QIAwell.

FIG. 3 shows an arrangement, wherein the device of the invention, consisting of a three-layered filter 20, 21, 22, is attached onto a cartridge, wherein between two means 5 and 6, an anion exchanger material is present. The sample to be separated is layered on top of filter layer 20, and the filter head is attached onto the cartridge (substantially, a likewise cylindrical hollow body) 1 (extraction column). Thereafter, the solution to be separated passes the filter unit 70, optionally by applying slightly elevated or reduced pressure, and drips into the container (extraction column) beneath, wherein the anion exchanger material 10 is arranged. Then, under suitable buffer conditions (low salt concentration), nucleic acids, for instance, bind to the anion exchanger material. Cell debris is located in the filter head 40 of the invention, whereas the nucleic acids of interest are present adsorbed to the ion exchangers. Subsequent to discarding the filter cake in the filtration unit 40, the cylindrical hollow body 1 containing the nucleic acids may be further processed.

FIG. 4 shows an analogous situation as in FIG. 3 with the filter head 40 of the invention, wherein a two-layered filter sealed by a hydrophobic interlayer 23 is used. Preferably, the outlet opening 60 of the device according to the invention is dimensioned such that it may be shoved into the corresponding cartridge 1 of the material adsorbing nucleic acids, and is secured there due to frictional forces.

Likewise, the filtration units illustrated in FIGS. 1, 2a) and 2b) may be attached onto a cartridge wherein a material capable of binding nucleic acids at high ionic strength is arranged. In particular, these are materials such as glass, silica gel and other mineral substances. Then, for example, a nucleic acid preparation may be conducted under high salt conditions. The appropriately prepared and digested sample then is passed through a filtration unit of the invention according to one of the configurations of FIGS. 1, 2a) or 2b), and then, in device 1 illustrated in FIG. 5, is adsorbed to silica gel, glass fiber, pressed powdered glass materials 11 under conditions of high ionic strength.

Figure 5:
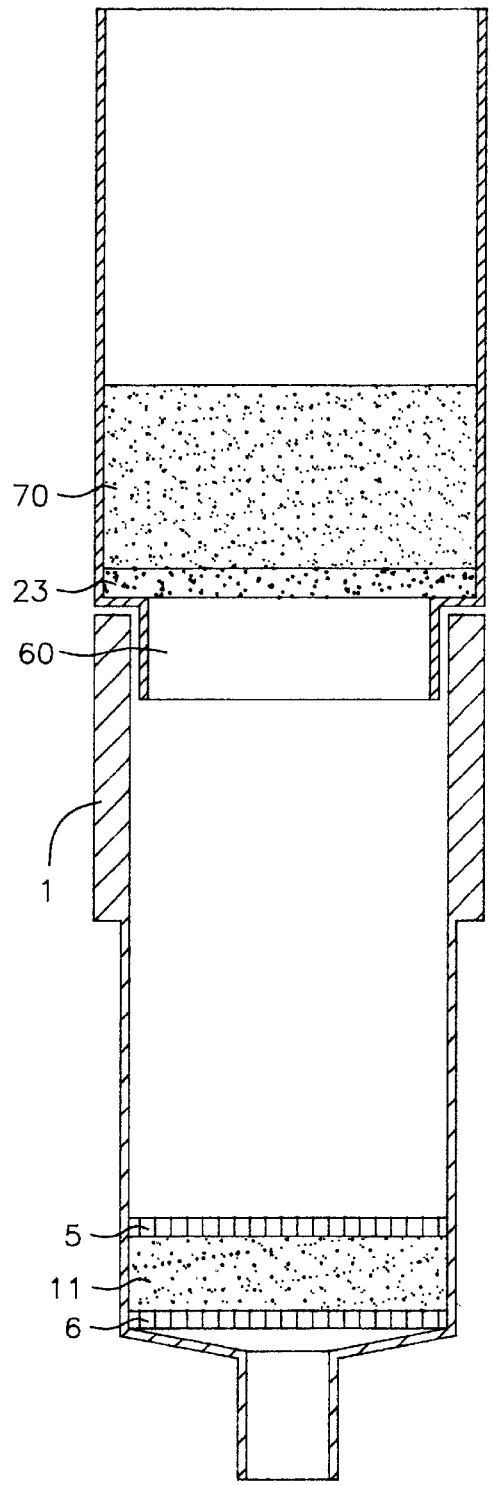
FIG. 5 shows the device of the invention with a filter layer having an asymmetric pore size distribution as viewed in the direction of sample flow.

FIG. 5 shows the device of the invention with a filter layer 70 having an asymmetric pore size distribution as viewed in the direction of sample flow. Here, the pore size decreases continuously or discontinuously from about 100–500 $\mu$m to 5–30 $\mu$m in flow direction. The pore size of the filter layer varies in the range of from 5 $\mu$m to 500 $\mu$m at a filter layer thickness of from 0.1 to 10 mm.

Figure 6:
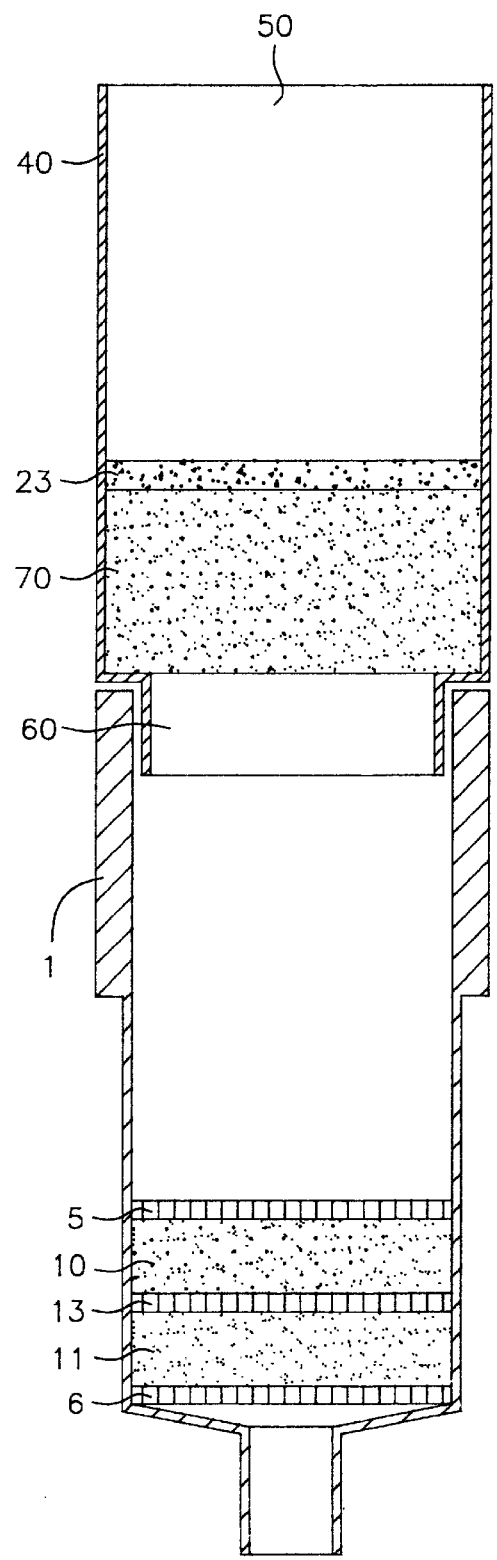
FIG. 6 shows an arrangement in a configuration similar to FIG. 5 on an extraction column wherein an anion exchanger material is arranged above the mineral support according to FIG. 5.

FIG. 6 shows an arrangement, wherein the device of the invention is arranged in a configuration similar to FIG. 5 on an extraction column, wherein an anion exchanger material 10 is arranged above the mineral support 11 according to FIG. 5. This arrangement is advantageous since the digested sample in the device of the invention is freed from cell debris and drips into the extraction column 1, to be adsorbed to the anion exchanger material 10 under low salt conditions. Subsequent to discarding the filter cake, the nucleic acid bound in the ion exchanger may first be washed under conditions of low ionic strength and then eluted from the anion exchanger 10 under conditions of high ionic strength. Subsequently, the nucleic acid eluted from the anion exchanger under high salt conditions is adsorbed by the inorganic material 11, e.g., silica gel or glass fiber. Following further washing steps, the RNA may then be desorbed and eluted from the support 11 by adding distilled water, for example.

Figure 7:
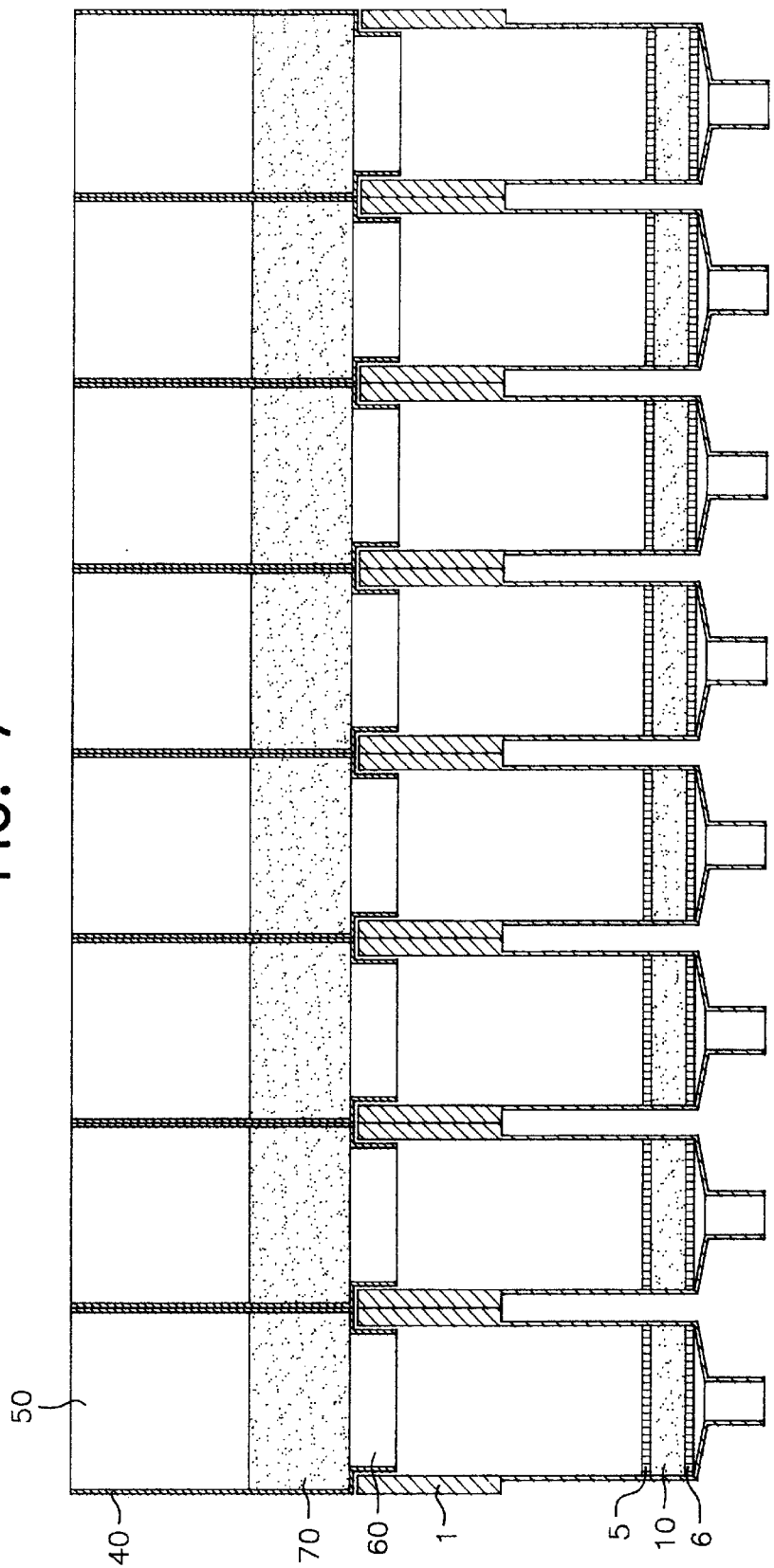
FIG. 7 illustrates another preferred embodiment of the device according to the invention which may be present in the form of microtitration strips.

FIG. 7 illustrates another preferred embodiment of the device according to the invention, which may be present in the form of microtitration strips. FIG. 7 shows an arrangement, wherein the device of the invention 40, arranged in linear succession, is already arranged on an appropriate arrangement as described in FIG. 3, for example. The hydrophobic layer 23 may be arranged beneath or above the filtration unit.

Figure 8:
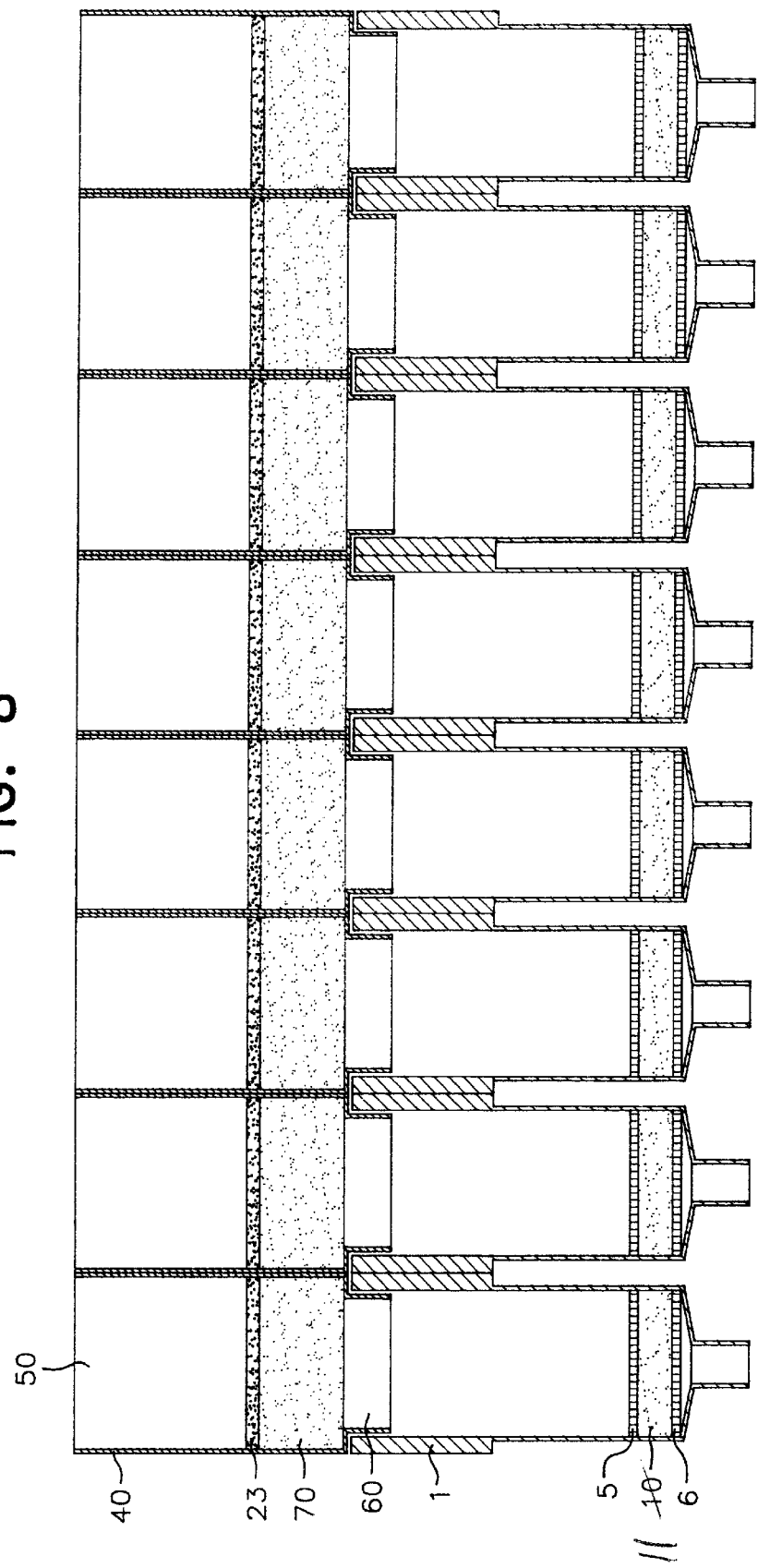
FIGS. 8 and 9 show corresponding configuration having different adsorption materials.
Figure 9:
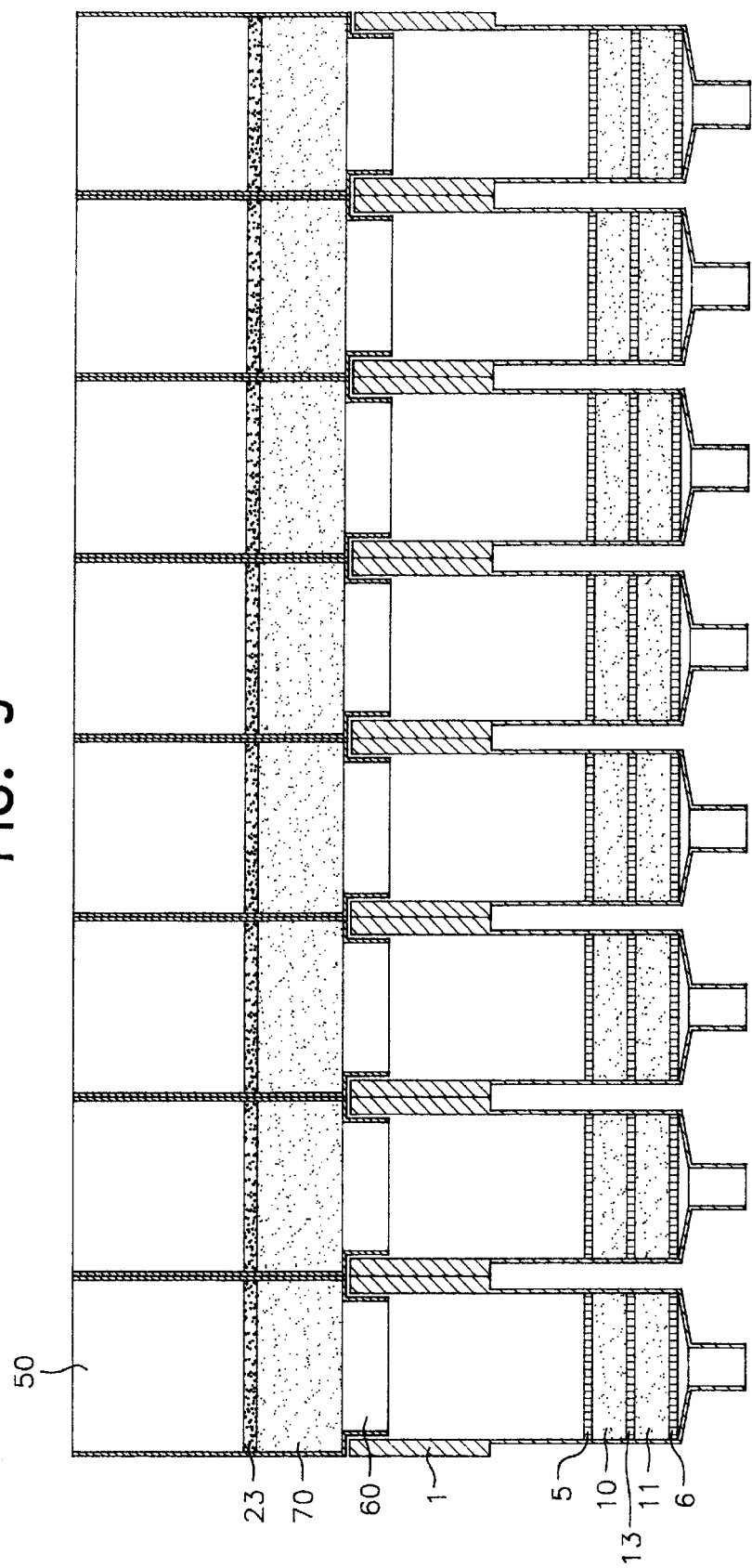

In FIGS. 8 and 9, corresponding configurations each having different adsorption materials are described.

The invention will be illustrated in more detail by the following Examples.

EXAMPLE 1

Plasmid Minipreparation

A 1.5 ml HB 101 *E. coli* culture with pUC 18 plasmid DNA in LB medium is centrifuged at 3,000 g for 5 minutes to pelletize the cells. The cell pellet is resuspended in 0.25 ml of 50 mM Tris-HCl, 10 mM EDTA, pH 8.0, 100 $\mu$g/ml of RNase A. For cell lysis, 0.6 ml of 0.2 M NaOH and 1% SDS are added to the cell suspension, mixed carefully, and allowed to stand at room temperature for 5 minutes. This is followed by neutralization using 0.25 ml of 3 M potassium acetate, 2 M acetic acid, mixing and incubation on ice for 15 minutes. The lysate is transferred to the filtration device according to FIG. 1. The entire device is attached on top of a vacuum chamber, and the cell lysate is sucked through the device at a pressure difference of 20–800 mbars into a 2 ml vial. Alternatively, the sample may be pressed through the filtration layers using a piston or elevated pressure. Following filtration, the filtration device is detached, and the filter cake, together with cell fragments, denatured proteins and precipitated SDS, is discarded. The DNA in the filtrate is precipitated with 0.5 volumes of isopropanol, and the alcoholic pellet is pelletized by centrifugation.

Where the design of the filtration device according to the invention is in microtiter formate, up to 96 samples may be processed at the same time. Thus, the time required to prepare 96 samples may be reduced from 240 minutes to 15 minutes.

EXAMPLE 2

Plasmid Minipreparation on Anion Exchanger

A 1.5 ml HB 101 *E. coli* culture with pUC 18 plasmid DNA in LB medium is centrifuged at 3,000 g for 5 minutes to pelletize the cells. The cell pellet is resuspended in 0.25 ml of 50 mM Tris-HCl, 10 mM EDTA, pH 8.0, 100 $\mu$g/ml of RNase A. For cell lysis, 0.25 ml of 0.2 M NaOH and 1% SDS are added to the cell suspension, mixed carefully, and allowed to stand at room temperature for 5 minutes. This is followed by neutralization using 0.25 ml of 3 M potassium acetate, 2 M acetic acid, mixing and incubation on ice for 15 minutes. The lysate is transferred to the filtration device according to FIG. 3. The entire device is attached on top of a vacuum chamber, and the cell lysate is sucked through the device of the invention at a pressure difference of 20–800 mbars and filtrated onto an anion exchanger column. Alternatively, the sample may be pressed through the filtration layers using a piston or elevated pressure. Following filtration, the filtration device is detached, and the filter cake, together with cell fragments, denatured proteins and precipitated SDS, is discarded. The filtrate is sucked or forced through the extraction column completely to achieve adsorption of DNA. Subsequently, the extraction column is washed twice with 1 ml of 1 M NaCl, 15% ethanol, 50 mM MOPS, pH 7.0, to remove RNA and proteins. The DNA is eluted with 1 ml of 1,25 M NaCl, 15% ethanol, 50 mM Tris-HCl, pH 8.5. For desalting and concentrating, the eluted DNA is precipitated with alcohol, and the alcoholic pellet is pelletized by centrifugation.

EXAMPLE 3
Plasmid Minipreparation with Cell Lysis in the Filter

A 1.5 ml HB 101 *E. coli* culture with pUC 18 plasmid DNA in LB medium is centrifuged at 3,000 g for 5 minutes to pelletize the cells. The cell pellet is resuspended in 0.25 ml of 50 mM Tris-HCl, 10 mM EDTA, pH 8.0, 100 µg/ml of RNase A and transferred to the filtration device according to FIG. 4. For cell lysis, 0.25 ml of 0.2 M NaOH and 1% SDS are added to the cell suspension is placed into the filtration device according to FIG. C, the device is sealed with a stopper or an adhesive film and is allowed to stand at room temperature for 5 minutes. This is followed by addition of 0.25 ml of 3 M potassium acetate, 2 M acetic acid for neutralization, the device is sealed with a stopper or an adhesive film, mixed carefully and incubated on ice for 15 minutes. Due to the hydrophobic interlayer, early outflow of the lysing reagents through the filter layer is avoided, and cell lysis is possible directly in the filter unit. The entire device is attached on top of a vacuum chamber, and the cell lysate is sucked through the device at a pressure difference of 20–800 mbars. Alternatively, the sample may be pressed through the filtration layers using a piston or elevated pressure. Following filtration, the filtration device is detached, and the filter cake, together with cell fragments, denatured proteins and precipitated SDS, is discarded. The extraction column is washed twice with 0.8 ml of 1 M NaCl, 15% ethanol, 50 mM MOPS, pH 7.0, to remove RNA and proteins. The DNA is eluted with 1 ml of 1.25 M NaCl, 15% ethanol, 50 mM Tris-HCl, pH 8.5. For desalting and concentrating, the eluted DNA is precipitated with alcohol, and the alcoholic pellet is pelletized by centrifugation.

EXAMPLE 4
Plasmid Minipreparation on Silica Gel

A 1.5 ml HB 101 *E. coli* culture with pUC 18 plasmid DNA in LB medium is centrifuged at 3,000 g for 5 minutes to pelletize the cells. The cell pellet is resuspended in 0.25 ml of 50 mM Tris-HCl, 10 mM EDTA, pH 8.0, 100 µg/ml of RNase A. For cell lysis, 0.25 ml of 0.2 M NaOH and 1% SDS are added to the cell suspension, mixed carefully and allowed to stand at room temperature for 5 minutes. This is followed by addition of 0.5 ml of 4.5 M guanidine-HCl, 0.75 M potassium acetate, pH 5.5, for neutralization, mixing and incubation on ice for 15 minutes. The entire device according to FIG. 5 is attached on top of a vacuum chamber, and the cell lysate is sucked at 20–800 mbars through the device into a test tube. In the test tube are placed 10 mg of a mineral support, e.g., silica gel or glass having a particle size of 1–5 µm in 0.1 ml of 4.5 M guanidine-HCl, 0.75 M potassium acetate, pH 5.5, which is able to adsorb the DNA under such conditions. Alternatively, the sample may be pressed through the filtration layers using a piston or elevated pressure. Following filtration, the filtration device is detached, and the filter cake, together with cell fragments, denatured proteins and precipitated SDS, is discarded.

The filtrate with DNA in high salt and the mineral support in high salt is incubated for 1–5 minutes to achieve adsorption of the DNA. The suspension is centrifuged at 3,000 rpm for 5 minutes, and the supernatant is discarded. The suspension is resuspended in 1 ml of 80% ethanol, 10 mM Tris-HCl, pH 7.0 and centrifuged again, and the pellet with bound DNA is dried on air at room temperature for 5 minutes. Eventually, the DNA is eluted with 100 µl of 10 mM Tris-HCl, pH 8.0. The eluted DNA may be used directly in enzymatic reactions such as, e.g., restriction, labeling, sequencing, or amplification.

EXAMPLE 5
Plasmid Minipreparation on Glass Membrane

A 1.5 ml HB 101 *E. coli* culture with pUC 18 plasmid DNA in LB medium is centrifuged at 3,000 g for 5 minutes to pelletize the cells. The cell pellet is resuspended in 0.25 ml of 50 mM Tris-HCl, 10 mM EDTA, pH 8.0, 100 µg/ml of RNase A. For cell lysis, 0.25 ml of 0.2 M NaOH and 1% SDS are added to the cell suspension, mixed carefully and allowed to stand at room temperature for 5 minutes. This is followed by addition of 0.5 ml of 4.5 M guanidine-HCl, 0.75 M potassium acetate, pH 5.5, for neutralization, mixing and incubation on ice for 15 minutes. The entire device according to FIG. 5 is attached on top of a vacuum chamber, and the cell lysate is sucked through the device at 20–800 mbars. Alternatively, the sample may be pressed through the filtration layers using a piston or elevated pressure. Following filtration, the filtration device is detached, and the filter cake, together with cell fragments, denatured proteins and precipitated SDS, is discarded. The filtrate with DNA in high salt and the mineral support in high salt is sucked or forced through the silica gel extraction column having, e.g., a glass fiber membrane 2 mm in thickness to achieve adsorption of DNA. The extraction column is washed twice with 1 ml of 6.5 M guanidine-HCl, 10 mM Tris-HCl, pH 7.0, to remove RNA and proteins. The extraction column is washed twice with 1 ml of 80% ethanol, 10 mM Tris-HCl, pH 7.0 and once with 0.8 ml of 90% ethanol/water, and traces of ethanol are sucked off. Eventually, the DNA is eluted with 10 µl of 10 mM Tris-HCl, pH 8.0, and is collected in new 1.5 ml tubes. The eluted DNA may be used directly in enzymatic reactions such as, e.g., restriction, labeling, sequencing, or amplification.

EXAMPLE 6
Plasmid Minipreparation on Anion Exchanger/Glass Membrane

A 1.5 ml HB 101 *E. coli* culture with pUC 18 plasmid DNA in LB medium is centrifuged at 3,000 g for 5 minutes to pelletize the cells. The cell pellet is resuspended in 0.25 ml of 50 mM Tris-HCl, 10 mM EDTA, pH 8.0, 100 g/ml of RNase A and transferred to a device according to FIG. 6. For cell lysis, 0.25 ml of 0.2 M NaOH and 1% SDS are added to the cell suspension, mixed carefully and allowed to stand at room temperature for 5 minutes. This is followed by addition of 0.25 ml of 3 M potassium acetate, 2 M acetic acid for neutralization, the device is sealed with a stopper or an adhesive film, mixed carefully and incubated on ice for 15 minutes. Due to the hydrophobic interlayer, early outflow of the lysing reagents through the filter layer is avoided, and cell lysis is possible directly in the filter unit.

The entire device is attached on top of a vacuum chamber, and the cell lysate is sucked through the device at a pressure difference of 20–800 mbars. Alternatively, the sample may be pressed through the filtration layers using a piston or elevated pressure. Following filtration, the filtration device is detached, and the filter cake, together with cell fragments, denatured proteins and precipitated SDS, is discarded. The extraction column is washed with 0.8 ml of 1 M NaCl, 15% ethanol, 50 mM MOPS, pH 7.0, and with 0.8 ml of 1 M NaClO$_4$, 15% ethanol, 10 mM sodium acetate, pH 7.0, to remove RNA and proteins. The DNA is eluted from the anion exchanger layer (10) using 7 M NaClO$_4$, 5% ethanol, 10 mM Tris-HCl, pH 7.0, and thereby, directly bonded to the silica gel layer (11). The extraction column is washed twice with 0.8 ml of 80% ethanol, 100 mM NaCl, 10 mM sodium acetate, pH 7.0, and with 0.8 ml of 90% ethanol/water. The ethanol/H$_2$O residues present in the extraction layer are volatilized by sucking through ambient air by vacuum for 1–2 minutes. Subsequently, the samples are eluted with each 100 l of 1 mM Tris-HCl, pH 8.0, and are collected in new 1.5 ml tubes. The eluted DNA may be used directly in enzymatic reactions such as, e.g., restriction, labeling, sequencing, or amplification.

EXAMPLE 7
Plasmid Minipreparation in a "Microtitration Strip"

8×1.5 ml of XL Blue *E. coli* cultures with pUC 18 plasmid DNA in LB medium is centrifuged at 3,000 g for 5 minutes to pelletize the cells. The cell pellets are resuspended in 0.25 ml of 50 mM Tris-HCl, 10 MM EDTA, pH 8.0, 100 g/ml of RNase A and transferred to the device according to FIG. 7. For cell lysis, 0.25 ml of 0.2 M NaOH and 1% SDS are added to the cell suspension into the filtration device, the device is sealed with a stopper or an adhesive film, mixed carefully and allowed to stand at room temperature for 5 minutes. This is followed by addition of 0.25 ml of 3 M potassium acetate, 2 M acetic acid for neutralization, careful mixing and incubating on ice for 15 minutes. The entire device is attached on top of a vacuum chamber, and the cell lysate is sucked through the device at 20–800 mbars. Alternatively, the sample may be pressed through the filtration layers by elevated pressure. Following filtration, the filtration device is detached, and the filter cake, together with cell fragments, denatured proteins and precipitated SDS, is discarded. The extraction column is washed with 0.8 ml of 1 M NaCl, 15% ethanol, 50 mM MOPS, pH 7.0, to remove RNA and proteins. The DNA is eluted with 8×1 ml of 1.25 M NaCl, 15% ethanol, 50 mM Tris-HCl, pH 8.5. For desalting and concentrating, the eluted DNA is precipitated with alcohol, and the alcoholic pellet is pelletized by centrifugation.

EXAMPLE 8
Plasmid Minipreparation in a "Microtitration Strip"

8×1.5 ml of LX Blue *E. coli* culture with pUC 18 plasmid DNA in LB medium is centrifuged at 3,000 g for 5 minutes to pelletize the cells. The cell pellets are resuspended in 0.25 ml of 50 mM Tris-HCl, 10 mM EDTA, pH 8.0, 100 g/ml of RNase A and transferred into the device according to FIG. 8. For cell lysis, 0.25 ml of 0.2 M NaOH and 1% SDS are added to the cell suspension into the filtration device, the device is sealed with a stopper or an adhesive film, mixed carefully and allowed to stand at room temperature for 5 minutes. This is followed by addition of 0.5 ml of 4.5 M guanidine-HCl, 0.75 M potassium acetate, pH 5.5, for neutralization, mixing and incubation on ice for 15 minutes. The entire device according to FIG. 9 is attached on top of a vacuum chamber, and the cell lysate is sucked through the device at 20–800 mbars. Alternatively, the sample may be pressed through the filtration layers using a piston or elevated pressure. Following filtration, the filtration device is detached, and the filter cake, together with cell fragments, denatured proteins and precipitated SDS, is discarded. The filtrate with DNA in high salt is sucked or forced through the silica gel extraction column to achieve adsorption of DNA. The extraction column is washed once with 1 ml of 6.5 M guanidine-HCl, 10 mM sodium acetate, pH 7.0, to remove RNA and proteins. The extraction column is washed twice with 1 ml of 80% ethanol, 10 mM Tris-HCl, pH 7.0 and with 0.8 ml of 90% ethanol/water, and traces of ethanol are sucked through. Eventually, the DNA is eluted with 100 l of 10 mM Tris-HCl, pH 8.0, and is collected in new 1.5 ml tubes. The eluted DNA may be used directly in enzymatic reactions such as, e.g., restriction, labeling, sequencing, or amplification.

EXAMPLE 9
Plasmid Minipreparation in a "Microtitration Strip" with Ion Exchanger and Glass Membrane 8×1.5 ml of XL Blue *E. coli* culture with pUC 18 plasmid DNA in LB medium is centrifuged at 3,000 g for 5 minutes to pelletize the cells. The cell pellets are resuspended in 0.25 ml of 50 mM Tris-HCl, 10 mM EDTA, pH 8.0, 100 g/ml of RNase A and are transferred to the device according to FIG. 9. For cell lysis, 0.25 ml of 0.2 M NaOH and 1% SDS are added to the cell suspension into the filtration device, the device is sealed with a stopper or an adhesive film, mixed carefully, and allowed to stand at room temperature for 5 minutes. This is followed by addition of 0.25 ml of 3 M potassium acetate, 2 M acetic acid for neutralization, mixing and incubation on ice for 15 minutes. The entire device is attached on top of a vacuum chamber, and the cell lysate is sucked through the device at 20–800 mbars. Alternatively, the sample may be pressed through the filtration layers using elevated pressure. Following filtration, the filtration device is detached, and the filter cake, together with cell fragments, denatured proteins and precipitated SDS, is discarded. The extraction column is washed with 0.8 ml of 1 M NaCl, 15% ethanol, 50 mM MOPS, pH 7.0, and with 0.8 ml of 1 M NaClO$_4$, 15% ethanol, 10 mM sodium acetate, pH 7.0, to remove RNA and proteins. The DNA is eluted from the anion exchanger layer using 7 M NaClO$_4$, 5% ethanol, 10 mM Tris-HCl, pH 7.0, and thereby, directly bonded to the silica gel layer. The extraction column is washed with 8×0.8 ml of 80% ethanol, 100 mM NaCl, 10 mM sodium acetate, pH 7.0, and with 8×0.8 ml of 90% ethanol/water. The ethanol/H$_2$O residues present in the extraction layer are volatilized by sucking through ambient air by vacuum for 1–2 minutes. Subsequently, the 8 samples are eluted with each 10 l of 1 mM Tris-HCl, pH 8.0.

EXAMPLE 10
Preparation of Genomic DNA 100 mg of rat liver tissue is comminuted to pieces 1 mm in size using a scalpel and suspended in 1 ml of 500 mM guanidine-HCl, 50 mM Tris-HCl, 10 mM EDTA, pH 8.0, and the cells are lysed at 50° C. for 2 hours by addition of 0.1 ml of proteinase K (10 mg/ml). The lysate is transferred into the filtration device according to FIG. 9. The entire device is attached on top of a vacuum chamber, and the cell lysate is sucked through the device at 20–800 mbars. Alternatively, the sample may be pressed through the filtration layers using elevated pressure. Following filtration, the filtration device is detached, and the filter cake, together with cell fragments and denatured proteins, is discarded. The extraction column is washed with 0.8 ml of 1 M NaCl, 15% ethanol, 50 mM MOPS, pH 7.0, and with 0.8 ml of 1 M NaClO$_4$, 15% ethanol, 10 mM sodium acetate, pH 7.0, to remove RNA and proteins. The DNA is eluted from the anion exchanger layer (10) using 7 M NaClO$_4$, 5% ethanol, 10 mM Tris-HCl, pH 7.0, and thereby, directly bonded to the silica gel layer (11). The extraction column is washed with 8×0.8 ml of 80% ethanol, 100 mM NaCl, 10 mM sodium acetate, pH 7.0, and with 8×0.8 ml of 90% ethanol/water. In order to remove the high salt solution, the test tubes are washed with 0.8 ml of 70% ethanol, 100 mM NaCl, 10 mM sodium acetate, pH 7.0, and with 8×0.8 ml of 90% ethanol/water. The ethanol/H$_2$O residues present in the extraction layer are volatilized by sucking through ambient air by vacuum for 1–2 minutes. Subsequently, the 8 samples are eluted with each 50 l of 1 mM Tris-HCl, 0.1 mM EDTA, pH 8.0.

EXAMPLE 11

Preparation of Genomic DNA with Filtration and Glass Membrane 100 mg of rat liver tissue is comminuted to pieces 1 mm in size using a scalpel and suspended in 1 ml of 500 mM guanidine-HCl, 50 mM Tris-HCl, 10 mM EDTA, pH 8.0, and the cells are lysed at 50° C. for 2 hours by addition of 0.1 ml of proteinase K (10 mg/ml). This followed by addition of 0.5 ml of 5 M guanidine-HCl, 10 mM Tris-HCl, pH 7 or 0.25 ml of ethanol and mixing to adjust the sample to the adsorption conditions on glass. The entire device according to FIG. 9 is attached on top of a vacuum chamber, and the cell lysate is sucked through the device at 20–800 mbars. Alternatively, the sample may be pressed through the filtration layers using a piston or elevated pressure. Following filtration, the filtration device is detached, and the filter cake, together with cell fragments, is discarded. The filtrate with DNA in high salt or in ethanol is sucked or forced through the silica gel extraction column with a glass fiber membrane 2 mm in thickness to achieve adsorption of DNA. The extraction column is washed once with 1 ml of 5 M guanidine-HCl, 10 mM Tris-HCl, pH 7.0, to remove RNA and proteins. The extraction column is washed twice with 1 ml of 80% ethanol, 10 mM Tris-HCl, pH 7.0 and with 0.8 ml of 90% ethanol/water, and traces of ethanol are sucked through. Eventually, the DNA is eluted with 100 l of 10 mM Tris-HCl, pH 8.0, and is collected in new 1.5 ml tubes. The eluted genomic DNA may be used directly in an enzymatic reaction such as, e.g., restriction, labeling, sequencing, or amplification.

What is claimed is:

1. A device useful for isolating cell components from a sample of digested cells, the device comprising:

a) a hollow body having inlet and outlet openings;

b) a filtration unit disposed inside said hollow body and comprising a filter sheet having multiple layers with pore size decreasing in the direction from the inlet to the outlet openings, wherein the pore size is 5–500 μm, and the filter sheet has a thickness of 0.1–10 mm; and c) an anion exchange material disposed in said hollow body and arranged downstream of, and in cooperation with, said filtration unit.

2. The device of claim 1 wherein the hollow body is cylindrical.

3. The device of claim 1 wherein said filtration unit further comprises a hydrophobic interlayer above or beneath the filter sheet.

4. A microtitration assembly having multiple elements, each of said elements comprising a device according to claim 1, and said elements are arranged parallel to one another in a single unit.

* * * * *